US012088221B2

(12) United States Patent
Regnier et al.

(10) Patent No.: US 12,088,221 B2
(45) Date of Patent: Sep. 10, 2024

(54) PIEZOELECTRIC ENERGY HARVESTER WITH A CONTROLLED DEFLECTION BEAM, IN PARTICULAR FOR POWERING A LEADLESS AUTONOMOUS CARDIAC CAPSULE

(71) Applicant: CAIRDAC, Antony (FR)

(72) Inventors: Willy Regnier, Longjumeau (FR); An Nguyen-Dinh, La Riche (FR); Julien Dohin, Vanves (FR)

(73) Assignee: CAIRDAC, Antony (FR)

( * ) Notice: Subject to any disclaimer, the term of this patent is extended or adjusted under 35 U.S.C. 154(b) by 44 days.

(21) Appl. No.: 18/151,579

(22) Filed: Jan. 9, 2023

(65) Prior Publication Data

US 2023/0369994 A1    Nov. 16, 2023

(30) Foreign Application Priority Data

May 10, 2022   (EP) ..................................... 22315101

(51) Int. Cl.
  *H02N 2/18*      (2006.01)
  *A61N 1/375*     (2006.01)
  *A61N 1/378*     (2006.01)

(52) U.S. Cl.
  CPC ........... *H02N 2/186* (2013.01); *A61N 1/3756* (2013.01); *A61N 1/3785* (2013.01)

(58) Field of Classification Search
  CPC .............................. H02N 2/186; H10N 30/306
  See application file for complete search history.

(56) References Cited

U.S. PATENT DOCUMENTS

| 2019/0247050 | A1* | 8/2019  | Goldsmith | A61F 2/82   |
| 2019/0381325 | A1* | 12/2019 | Regnier   | A61N 1/37518|
| 2020/0338241 | A1* | 10/2020 | Regnier   | A61N 1/37229|
| 2021/0153842 | A1* | 5/2021  | Makdissi  | A61B 8/12   |
| 2022/0203102 | A1* | 6/2022  | Makdissi  | A61N 1/0565 |
| 2022/0305272 | A1* | 9/2022  | Makdissi  | A61N 1/37518|

FOREIGN PATENT DOCUMENTS

FR    3082434 A1    12/2019
WO    2018-122244 A1    7/2018

OTHER PUBLICATIONS

European Patent Office, Search Report issued in corresponding Application No. EP 22 31 5101, dated Oct. 26, 2022.

* cited by examiner

*Primary Examiner* — Bryan P Gordon
(74) *Attorney, Agent, or Firm* — Stites & Harbison, PLLC; Jeffrey A. Haeberlin

(57) ABSTRACT

The module comprises, in an envelope tube, a pendular unit comprising a piezoelectric transducer, PZT, beam, an inertial mass coupled to the free end of the beam, and a beam mount secured to the tube and fastened to a clamping part of the beam. The module further includes a symmetrization insert for calibrating and symmetrizing the pendular unit oscillations in transverse and lateral directions. The symmetrization insert is distinct from the beam mount and comprises a peripheral portion secured to the tube independently of the beam mount, and a central portion with an axial through-cavity inside which the beam extends in said region of free travel. The axial cavity extends between opposite travel limitation surfaces, which are symmetrical and capable of coming into contact with the beam in a bending configuration of the beam.

7 Claims, 7 Drawing Sheets

PIEZOELECTRIC ENERGY HARVESTER WITH A CONTROLLED DEFLECTION BEAM, IN PARTICULAR FOR POWERING A LEADLESS AUTONOMOUS CARDIAC CAPSULE

BACKGROUND OF THE INVENTION

Technical Field

The invention relates to energy harvesting devices, also called "harvesters" or "scavengers", which collect the mechanical energy resulting from various movements they undergo and convert this mechanical energy into electrical energy.

It more particularly relates to the harvesting devices of the so-called "PEH" (Piezoelectric Energy Harvester) type, which use as a mechanical-electrical transducer an oscillating piezoelectric beam coupled to an inertial mobile mass.

The invention will be more particularly described in an application of such energy harvesters to autonomous medical devices, in particular devices of the autonomous implantable capsule type, in particular those which are intended to be implanted in a heart cavity.

This application, although being particularly advantageous, must however not be considered as limiting the invention, whose teachings can be applied to many other types of autonomous devices incorporating an energy harvester of the PEH type, whether these devices are implantable or not, medical or not.

State of the Art

In the field of medical implants, the recent advances in miniaturization of active devices and the advances in life sciences allow from now on the development of a wide variety of fully autonomous, miniaturized implantable systems, for monitoring, diagnosis or treatment purposes.

Such devices implement less invasive implantation procedures, provide more comfort, increased performances, and often open up access to new types of diagnoses and treatments.

When applied to the field of medical implants, the invention more particularly relates to those devices which incorporate a self-powering system comprising a mechanical energy harvester associated with an integrated energy storage component, such as a rechargeable battery or a high-performance capacitor.

Indeed, one of the critical aspects of these miniaturized devices is the power autonomy. The life duration of such an implant being of about 8-10 years, taking into account the very small dimensions, it is not possible to use a conventional battery, even a high-density one.

The energy harvesting device addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, heart tissue vibrations linked i.a. to closings and openings of the heart valves, or also blood flow rate variations in the surrounding environment, which stress the implant and make it oscillate at the rhythm of the flow rate variations.

The mechanical energy collected by the harvester is converted into electrical energy (voltage or current), by means of a suitable mechanical-electrical transducer, for powering the various circuits and sensors of the device and charging the energy storage component. This power supply system allows the device to operate in full power autonomy for its whole lifetime.

This energy harvesting technique is particularly well adapted for powering the implanted autonomous capsules having no physical connection with a remote device. Such capsules are called for this reason "leadless capsules", for distinguishing them from the electrodes or sensors arranged at the distal end of a lead, through the whole length of which run one or several conductors connected to a generator itself connected to the opposite, proximal end.

The invention is nevertheless not limited to a particular type of capsule, nor even of leadless implant, and is applicable as well to many other types of autonomous devices, whatever the operational purpose thereof, cardiac or other, medical or not.

In the cardiac application case, the leadless capsule continuously monitors the patient's rhythm and if necessary issues to the heart electrical pulses for pacing, resynchronization and/or defibrillation in case of rhythm disorders detected by the capsule. The capsule further comprises various electronic circuits, sensors, etc., as well as wireless communication transmission/reception means for the remote exchange of data, the whole being integrated in a body of very small size able to be implanted at sites of difficult access or leaving little available space, such as the ventricle apex, the inner wall of the atrium, etc.

WO 2019/001829 A1 (Cairdac), corresponding to U.S. Pat. No. 11,045,657 B2, as well as EP 3 693 056 A1 (Cairdac) and US 2018/185638 A1 (Regnier) describes examples of such leadless intracardial capsules.

The invention more particularly relates to capsules or similar implantable devices whose energy harvester is of the PEH type, i.e. using a Piezoelectric Transducer or "PZT" and an inertial pendular unit subjected to the external stresses described hereinabove. The inertial pendular unit comprises, within the capsule body, a mobile mass called "seismic mass" or "inertial mass", which is driven according to the movements of the capsule, permanently subjected to the various external stresses described hereinabove. After each of these stresses, the inertial mass, which is coupled to an elastically deformable element, oscillates at a natural free oscillation frequency.

The mechanical energy of the oscillation is converted into electrical energy by a mechanical-electrical transducer producing an electrical signal. This mechanical-electrical transducer may be in particular a PZT that is cyclically stressed in bending so as to generate within its constituent material electrical charges that are collected at the surface of the component to be used by the self-powering system of the leadless capsule. The PZT is most often in the form of a beam clamped at one of its end and coupled to the inertial mass at its other end, which is free.

The transducer output electrical signal is sent to a power management circuit of the capsule, which rectifies and regulates the electrical signal to output a stabilized direct voltage or current, usable to power the various electronic circuits and sensors of the capsule, and to charge the energy storage component.

The mechanical structure of such an energy harvester of the PEH type is described in detail in particular in WO 2018/122244 A1 (Sorin CRM/Regnier). US 2019/381325 A1 (Regnier et al.) also describes a multifunction part ensuring among other things the positioning and the holding of the different elements of the pendular unit.

It will be noted that the term "beam" has to be understood in its broadest sense, i.e. an elongated, thin and flat strip, it being understood that the shape of this strip is not necessarily rectangular nor its thickness constant (as in the description of the particular embodiment that will be given hereinafter). Within the meaning of the present invention, the term "beam" hence covers elements that may have a non-constant width and/or thickness in the longitudinal direction, as well as, possibly, a deformability liable to exceed a unique degree of freedom in bending.

The problem of the invention is that it is difficult to benefit from the maximum potentially available oscillation amplitude of the PZT.

This oscillation amplitude determines the quantity of energy that is effectively harvestable by the PEH. Indeed, the charges that are produced by the bending of the beam, and collected by the management and regulating circuit of the PEH, are all the higher as the bending is great, and thus the deflection of the pendular unit is high.

However, to ensure sufficient longevity, particularly in view of the lifespan of a heart implant (at least ten years without failure), this deformation, hence the oscillation amplitude of the pendular unit, is restricted to a value ensuring a fatigue-less operation of the PZT materials, even in the very long term.

In practical terms, in the example of a PEH integrated to a leadless capsule whose structure is comparable to that described in above-mentioned WO 2018/122244 A1 and US 2019/381325 A1, the maximum travel of the inertial mass is limited to a value (at its center of gravity) that is lower than 1.5 mm with an accuracy of about 0.1 mm, not to penalize the reliability of the implant in the very long term.

The problem of the invention more specifically relates to the preservation of this maximum oscillation amplitude by avoiding it to be reduced by a sub-optimal positioning of the pendular unit in the body of the PEH module at the time of assembly of this module, in particular due to an imperfect positioning of the inertial mass.

Indeed, the known techniques for assembling PEH modules such as those described in above-mentioned WO 2018/122244 A1 and US 2019/381325 A1 may lead to slight offsets or misalignments of the inertial mass in its housing at the time of mounting the pendular unit (PZT beam provided at one end with its clamping part and at the other end with the inertial mass) into the support housing of the PEH module, with a correlative reduction of the maximum travel of the inertial mass and consequently of the PZT bending amplitude and hence of the quantity of harvestable electric charges produced by the beam.

In practical terms, it has been observed that a loss of 0.1 mm, or even only 50 µm, over a maximum travel of 0.8 mm of the inertial mass causes a noticeable loss of the total power harvested by the PEH for powering the circuits of the implant.

The object of the invention is to propose a new structure of PEH module, and a new method for assembling such a structure, which minimize the losses on the maximum oscillation amplitude of the PZT, and thus makes it possible to obtain the maximum potentially available power for the PEH with a strict centering of the inertial mass in its support housing.

SUMMARY OF THE INVENTION

To solve theses problems and achieve the above-mentioned objects, the invention proposes a PEH module comprising, in a manner known per se, in particular from above-mentioned WO 2018/122244 A1, an elongated envelope tube and, contained inside the tube, a pendular unit comprising: a piezoelectric transducer, PZT, beam, the beam extending in axial direction between a clamped proximal end and a free distal end, and being elastically deformable in bending; an inertial mass, coupled to the free distal end of the beam and mobile in transverse direction inside the tube; and a beam mount, adapted to be secured to the tube and fastened to a beam clamping part at the proximal end of the beam. The pendular unit is adapted to convert a mechanical energy produced by oscillations of the pendular unit under the effect of external stresses undergone by the module into an oscillating electrical signal collected by surface electrodes of the beam.

Characteristically of the invention, this module further comprises a symmetrization insert, for calibrating and symmetrizing in transverse and lateral directions the pendular unit oscillations, the symmetrization insert being arranged inside the tube in a region of free travel of the beam near the inertial mass. The symmetrization insert is distinct from the beam mount and comprises: a peripheral portion adapted to be secured to the tube independently of the beam mount, the tube having an inner shape mating with the outer shape of the peripheral portion at the place where the peripheral portion has to be secured; and a central portion with an axial through-cavity inside which the beam extends in said region of free travel, the axial cavity extending between opposite travel limitation surfaces, the travel limitation surfaces being symmetrical and being capable of coming into contact with the beam in a bending configuration of the beam.

According to various advantageous embodiments:
the symmetrization insert comprises a synthetic-material element comprising said central portion of the insert, and a metal-material element adapted to be welded to the tube at said peripheral portion of the insert, the synthetic-material and metal-material elements being mechanically secured to each other;
said peripheral portion of the symmetrization insert comprises a flat surface for the positioning in axial rotation of the symmetrization insert with respect to the tube, and the tube comprises a surface mating with the flat surface of the insert;
the symmetrization insert comprises at least one notch for holding an edge of at least one printed circuit board supported by the beam mount and by the symmetrization insert; and/or
the travel limitation surfaces of the central portion of the symmetrization insert have a mutual transverse spacing which increases in a direction away from the beam mount.

The invention has also for object a method for assembling a PEH module as hereinabove, comprising the following steps:
a) preparation of a first sub-set comprising a piezoelectric transducer, PZT, beam, with an inertial mass at a distal end of the beam and a clamping part at a proximal end;
b) preparation of a second sub-set comprising i) a beam mount adapted to receive the clamping part, ii) a symmetrization insert located at an axial distance from the beam mount and distinct from the beam mount, and iii) at least one printed circuit board arranged between the beam mount and the symmetrization insert, the symmetrization insert having a central portion with an axial through-cavity inside which the beam extends in said region of free travel, the axial cavity extending between opposite travel limitation surfaces, the travel limitation surfaces being symmetrical and being capable of coming into contact with the beam in a bending configuration of the beam;

c) preparation of a third sub-set by positioning the first sub-set prepared at step a) into the second sub-set prepared at step b);

d) positioning of the third sub-set in an elongated envelope tube, the tube having an inner shape mating with a peripheral portion of the symmetrization insert;

e) transverse and lateral centering of the inertial mass in the symmetrization insert;

f) definitive attachment of the symmetrization insert to the tube;

g) definitive attachment of the beam mount to the tube; and h) centering of the piezoelectric transducer with respect to the tube, and attachment of the clamping part to the beam mount.

According to various advantageous embodiments of this method:

the definitive attachments at steps f), g) and/or h) are weldings;

the method comprises a step, prior to step b), of obtaining the symmetrization insert by mechanical securing of a synthetic-material element to a metal-material element adapted to be subsequently welded to the tube at step f); and/or in this last case, the mechanical securing is a snap-riveting of a pin of the synthetic-material element into a bore of the metal-material element.

The invention also relates to an autonomous device incorporating in a device body a PEH module as hereinabove, and comprising:

an electronic unit;

a PEH module as hereinabove, outputting an electric signal;

a power management circuit adapted to rectify and regulate the electric signal produced by the PEH module, to output a stabilized direct power voltage or current; and an energy storage component for powering the electronic unit.

Said stabilized direct voltage or current provided by the power management circuit is used to power the electronic unit and/or to charge the energy storage component of the autonomous device.

In particular, this autonomous device can be an active medical device of the leadless capsule type, comprising a capsule body with an element for anchoring to a wall of a patient's organ, and in which the external stresses to which is subjected the pendular unit of the PEH module are stresses applied to the capsule body resulting from movements of said wall and/or from flow rate variations of a flow in the surrounding environment.

BRIEF DESCRIPTION OF THE DRAWINGS

An exemplary embodiment of the present invention will now be described with reference to the appended drawings, in which the same references denote identical or functionally similar elements throughout the figures.

DETAILED DESCRIPTION OF PREFERENTIAL EMBODIMENTS OF THE INVENTION

An exemplary embodiment of the device of the invention will now be described, in an application to an autonomous implantable capsule intended to be implanted into a heart cavity.

As indicated hereinabove, this particular application is given only as an example of embodiment and does not limit the invention, whose teachings can be applied to many other types of autonomous devices incorporating an energy harvester of the PEH type, whether these devices are implantable or not, medical or not.

Figure 1:
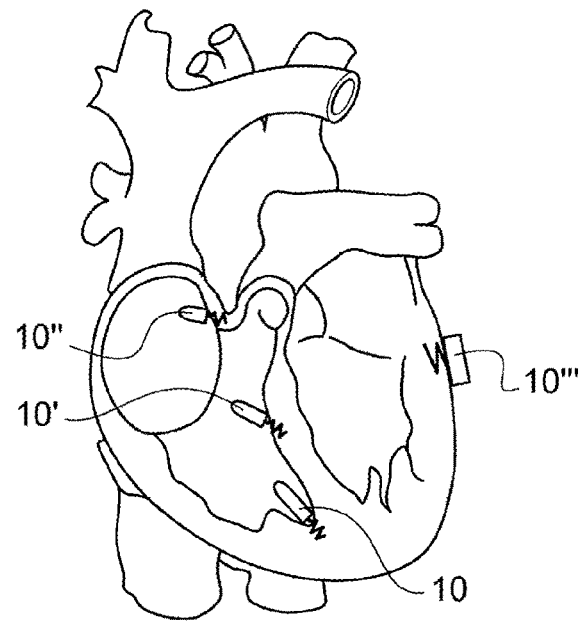
FIG. 1 illustrates medical devices of the leadless capsule type in their environment, with various examples of implantation sites in, on or near a patient's heart.

FIG. 1 shows various possibilities of implantation sites for a leadless type device in an application to cardiac pacing. Therefore, the capsule 10 is implanted inside a cavity of the myocardium (endocavitary implant), for example at the apex of the right ventricle. As an alternative, the capsule may also be implanted on the right interventricular septum, as in 10', or also on an atrial wall, as illustrated in 10". The device may also be an epicardial capsule placed on an external region of the myocardium, as illustrated in 10'''.

In any case, the leadless capsule is fixed to the heart wall by means of a protruding anchoring system intended to enter the heart tissue for the holding on the implantation site. Other anchoring systems can be used, and do not change in any way the implementation of the present invention.

Capsule 10 has the external form of an implant with an elongated tubular body 12 enclosing the various electronic and power supply circuits of the capsule, as well as an energy harvester with a pendular unit. The typical size of the known capsules is about 6 mm diameter for about 25 to 40 mm length.

Tubular body 12 has, at its front (distal) end 14, a protruding anchoring element, for example a helical screw 16, to hold the capsule on the implantation site. Other anchoring systems can be used, and do not change in any way the implementation of the present invention. The opposite (proximal) end 18 of capsule 10 is a free end, which is only provided with means (not shown) for the temporary connection to a guide-catheter or another implantation accessory used for implantation or explantation of the capsule, which is then detached from the latter.

Figure 2:
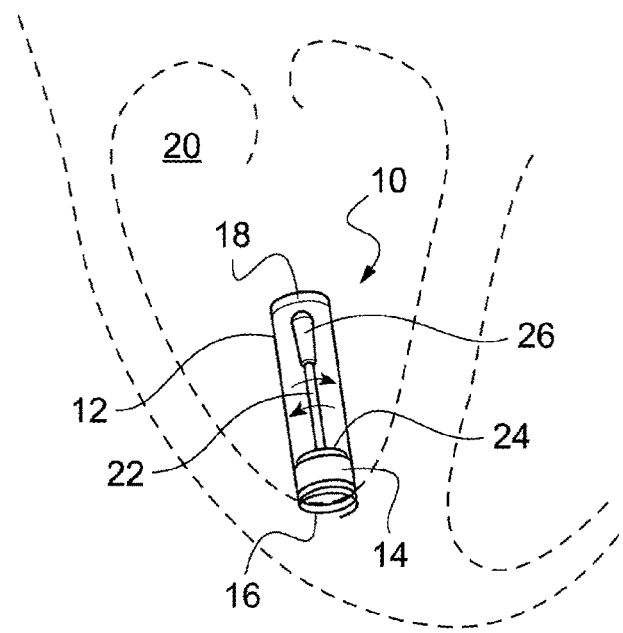
FIG. 2 illustrates a leadless capsule implanted in the bottom of the right ventricle of a patient.

In the example illustrated in FIG. 2, leadless capsule 10 is an endocavitary implant implanted into a cavity 20 of the myocardium, for example at the apex of the right ventricle. As an alternative, still in an application to cardiac pacing, the capsule can also be implanted on the interventricular septum or on an atrial wall, or also be an epicardial capsule placed on an external region of the myocardium, these different implantation modes not changing in any way the implementation of the present invention. To perform the detection/pacing functions, an electrode (not shown) in contact with the heart tissue at the implantation site collects the heart depolarization potentials and/or applies pacing pulses. In certain embodiments, the function of this electrode can be provided by anchoring screw 16, which is then an active screw, electrically conductive and connected to the detection/pacing circuit of the capsule.

Leadless capsule 10 is moreover provided with an energy harvesting module, called "PEH", comprising an inertial pendular unit that oscillates, inside the capsule, following the various external stresses to which the capsule is subjected. These stresses may result in particular from: movements of the wall to which the capsule is anchored, which are transmitted to tubular body 12 by anchoring screw 16; and/or blood flow rate variations in the environment surrounding the capsule, which produce oscillations of tubular body 12 at the rhythm of the heartbeats; and/or various vibrations transmitted by the heart tissues.

Figure 3:
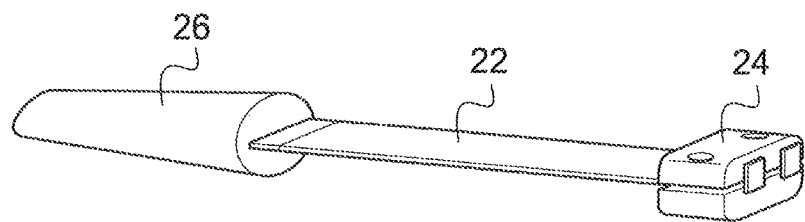
FIG. 3 shows in isolation a pendular unit of a known type, with a PZT in the form of an elongated beam clamped at one end and supporting an inertial mass at its opposite end.

The pendular unit, illustrated in isolation in FIG. 3, consists of a piezoelectric beam 22 attached to a clamping part 24 at one of its ends (hereinafter the "proximal end" of the beam), and whose opposite, free end (hereinafter the "distal end" of the beam) is coupled to a mobile inertial mass 26. Piezoelectric beam 22 is an elastically deformable flexible beam that constitutes, with inertial mass 26, a pendular system of the mass-spring type. Due to its inertia, mass 26 subjects beam 22 to a deformation of the vibratory type on either side of a neutral or non-deformed position corresponding to a stable rest position in the absence of any stress. The typical minimum size of the PZT beams of the known devices of this type is of the order of 25 mm long for about 5 mm width.

Actually, as for its mechanical behavior, this unit may be equated to a "clamped/free beam" structure, having a natural oscillation frequency, which is herein the frequency at which the mass-spring system oscillates.

It will be noted that this natural oscillation frequency, typically of the order of a few tens of hertz, is noticeably higher than the frequency of the external cyclic stresses that correspond to the heartbeat frequency (at most a few hertz). Hence, at each heart contraction, the inertial mass (or other functionally similar mechanical component) will be stressed with a higher or lower amplitude, then the pendular system will oscillate several times with decreasing amplitudes (bounces characteristic of a damped periodic oscillation), and will finally stabilize up to the following heartbeat, where the stress/oscillation cycle will be comparably repeated.

Beam 22 further performs, by piezoelectric effect, a mechanical-electrical transducer function for converting into electrical charges the mechanical bending stress that is applied to it. These charges are collected by electrodes at the surface of the beam to produce an electrical signal that, after rectification, stabilization and filtering, will power the electronic circuits of the capsule.

Figure 4:
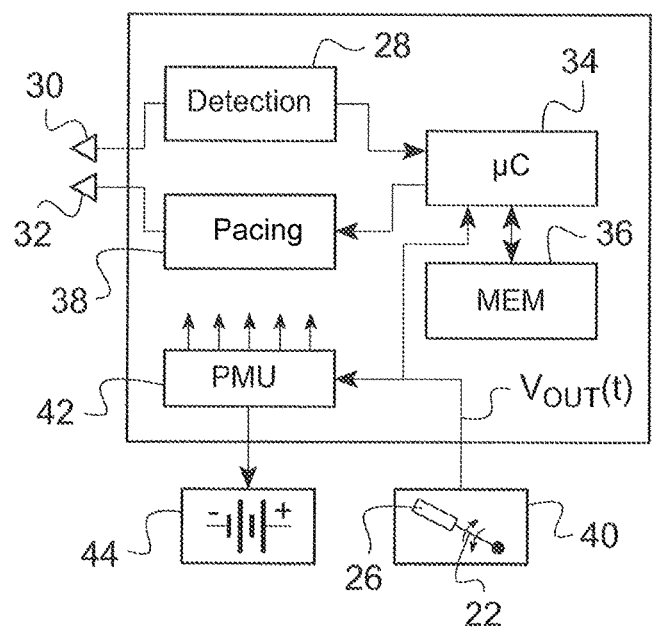
FIG. 4 schematically shows the main functional blocks of a leadless capsule.

FIG. 4 is a synoptic view of the various electric and electronic circuits integrated to the leadless capsule, presented as functional blocks.

Block 28 denotes a heart depolarization wave detection circuit, which is connected to a cathode electrode 30 in contact with the heart tissue and to an associated anode electrode 32, for example a ring electrode formed on the tubular body of the capsule. Detection block 28 comprises filters and means for analog and/or digital processing of the collected signal. The so-processed signal is applied to the input of a microcomputer 34 associated with a memory 36. The electronic unit also includes a pacing circuit 38 operating under the control of microcomputer 34 to provide to the system of electrodes 30, 32 myocardial pacing pulses.

An energy harvesting circuit or PEH 40 is moreover provided, which consists of the pendular unit formed by piezoelectric beam 22 and inertial mass 26, described hereinabove with reference to FIGS. 2 and 3. As piezoelectric beam 22 also ensures a mechanical-electrical transducer function, it converts into electrical charges the mechanical stresses undergone and produces a variable electrical signal $V_{OUT}(t)$, which is an alternating signal oscillating at the natural oscillation frequency of the pendular beam 22/mass 26 unit, and at the rhythm of the successive beats of the myocardium to which the capsule is coupled.

The variable electrical signal $V_{OUT}(t)$ is sent to a power management circuit or PMU 42. PMU 42 rectifies and regulates the signal $V_{OUT}(t)$ so as to output a stabilized direct voltage or current for powering the various electronic circuits and charging the integrated battery 44.

On the other hand, the beam is advantageously a beam of the bimorphous type, i.e. capable of generating energy on its two faces when subjected to a deformation. Theses transduction properties are typical of a piezoelectric material, such as PZT ceramics or PMN-PT, barium titanate or lithium niobate mono-crystals.

Figure 5:
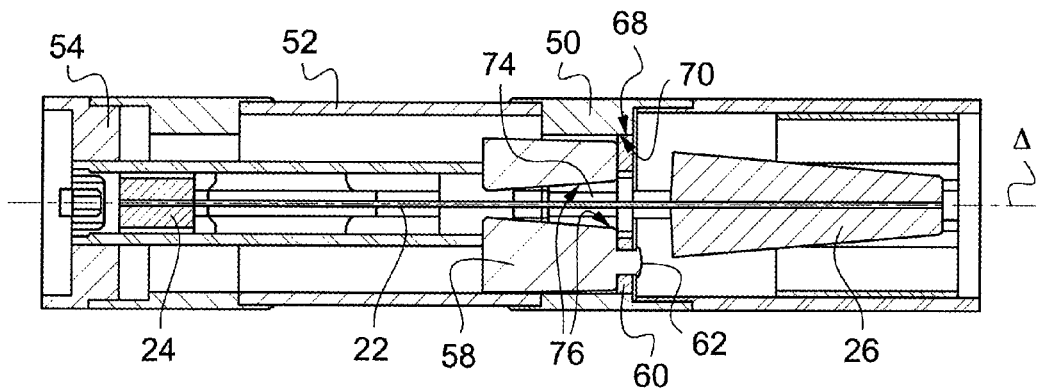
FIG. 5 is a cross-sectional view, along an axial plane, of the PEH module according to the invention.
Figure 6:
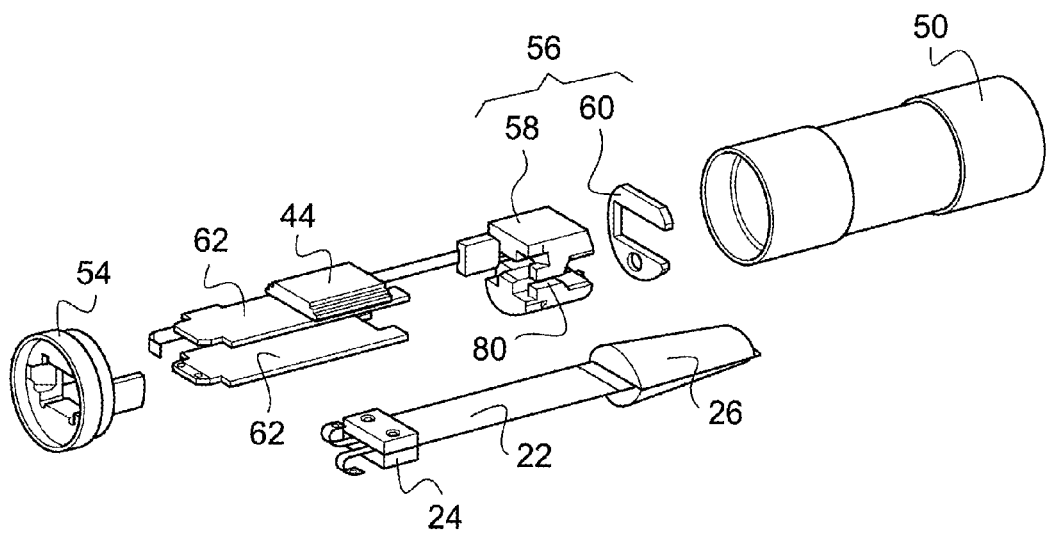
FIG. 6 is an exploded perspective view showing the different elements of the PEH module of FIG. 5.

In FIGS. 5 and 6 are shown the main elements of a PEH module according to the invention.

These different elements are contained inside an envelope tube 50, that is generally a metal tube (to allow welding operations that will be described hereinafter), preferably made of titanium due to the excellent biocompatibility of this metal.

An envelope tube particularly suitable for making a leadless capsule is described in particular in EP 3 730 185 A1 (Cairdac), corresponding to US 2020/338241 A1 (Regnier et al.), that illustrates in particular a metal/ceramic composite tube having a central portion (52 in FIG. 5) made of a radio-frequency transparent ceramic material, in such a way as to allow a wireless communication between electronic circuits located inside the tube and the outer environment, the rest of the tube being made of a metal material such as titanium, the whole forming a one-piece tubular unit.

Envelop tube 50 contains the pendular unit which consists of beam 22 held on the proximal side by clamping part 24 and carrying inertial mass 26 on the distal side. The pendular unit is placed at the center of envelope tube 50 and aligned on axis Δ of the tube.

In the following, it will be understood by "axial direction", the direction of greater length of the beam, and by "transverse direction", the direction of deformation of the beam, a direction that is located in a radial plane and that is perpendicular to the axial direction Δ; the direction perpendicular to the axial and transverse directions will be called "lateral direction".

Clamping part 24 is held in the tube by a mount 54 attached to the tube, in particular a mount made of a metal material such as titanium, capable of being peripherally welded to the tube in such a way as to attach mount 54, and hence clamp 24 and beam 22, to tube 50.

EP 3 892 325 A1 (Cairdac), corresponding to US 2021/316148 A1 (Regnier et al.), describes in detail an example of clamping part and mount, and reference can be made to this document for more details.

On the distal side of the beam, before inertial mass 26 and near to it, is arranged a characteristic part of the present invention, called hereinafter "symmetrization insert".

Symmetrization insert 56 is a part that is distinct from clamping part 24 and mount 54, unlike in particular the multifunction part described in above-mentioned US 2019/381325 A1, in which these two elements belong to a same one-piece synthetic-material part.

Symmetrization insert 56 consists of two elements 58, 60, namely a synthetic-material part 58 and a metal-material part 60 that will be described in more detail hereinafter with reference to FIGS. 7 to 9.

The tube 50 also contains one or several printed circuit boards (PCBs) 62, in the example illustrated two PCBs 62, one of which carries battery 44.

These two PCBs are connected to each other by a sheet of flexible conductors and supported at each of their ends, on distal side by insert 56 and on proximal side by mount 54, respectively.

The configuration of these PCBs on either side of beam 22, and the way they are connected by a flexible sheet and supported between a proximal element and a distal element are described in particular in above-mentioned US 2019/381325 A1, to which reference can be made for more details.

Figure 7:
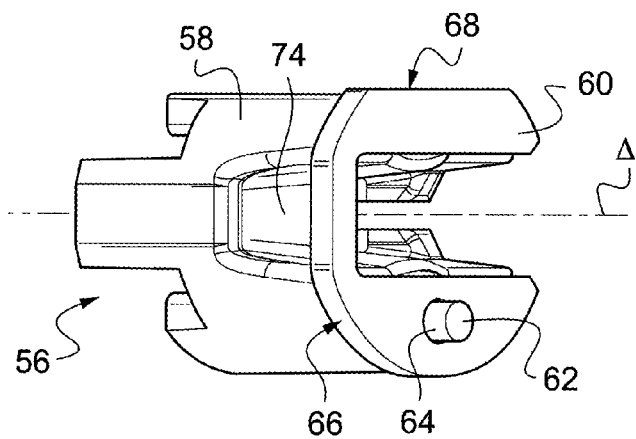
FIG. 7 is a three-quarter front perspective view showing in isolation the symmetrization insert characteristic of the PEH module according to the invention.
Figure 8:
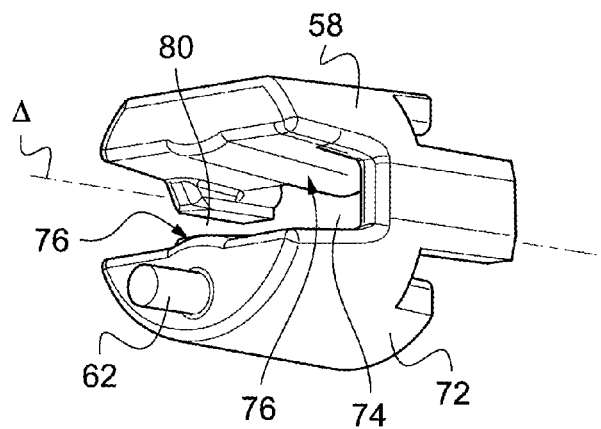
FIGS. 8 and 9 are three-quarter front and three-quarter back perspective views, respectively, of the synthetic-material part forming one of the elements of the symmetrization insert illustrated in FIG. 7.
Figure 9:
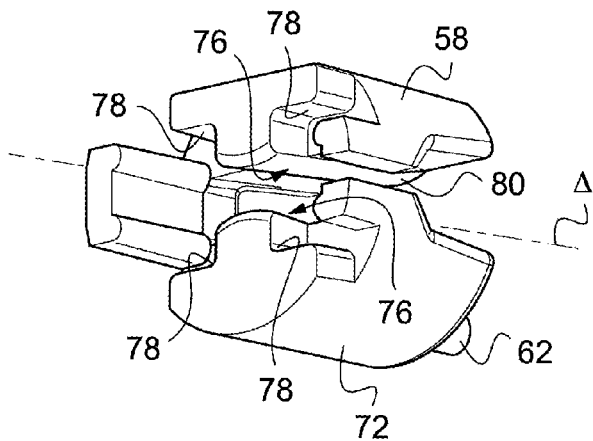

FIGS. 7 to 9 illustrate in more details the symmetrization insert 56 characteristic of the invention. FIG. 7 shows this insert in isolation, in perspective, with the two elements 58 and 60, respectively made of synthetic material and metal material, connected to each other, whereas FIGS. 8 and 9 show the synthetic-material part 58, in isolation, in three-quarter front and three-quarter back perspective.

The synthetic material of part 58 is a dielectric material such as a polyurethane thermoplastic polymer of the Tecothane® type or a polymer of the PET (polyethylene terephthalate) or PEEK (polyetheretherketone) type, or another plastic material that is injectable or made by other techniques, in particular by 3D printing from a dielectric polymer resin.

The metal material of part 60 is advantageously titanium, but it may also be a stainless steel, for example 316L steel, or also a metal such as tantalum or a nickel-titanium alloy of the nitinol type.

The two parts 58 and 60, which are made of materials of different natures, are mounted together and assembled by a mechanical method, for example by snap-riveting a pin 62 of synthetic-material part 58, inserted into a bore 64 of metal-material part 60.

Metal-material part 60 has an outer peripheral surface 66 sized in such a way that it can be assembled without a clearance inside a counterpart region of metal tube 50, whose inner surface mates with the shape of the peripheral surface 66 of part 60. Part 60 also includes a flat surface 68 for the positioning in axial rotation of part 60 inside the tube, this flat surface 68 cooperating with an inner surface 70 of mating shape of tube 50.

Once parts 58 and 60 mechanically assembled together, it will be possible to accurately adjust metal-material part 60, and consequently synthetic-material part 58, inside the tube, both in axial rotation (thanks to the flat surface 68) and in the transverse and lateral directions (through no-clearance cooperation between the outer surface 66 of part 60 and the mating cylindrical inner surface of tube 50).

Synthetic-material part 58, illustrated in isolation and in more detail in FIGS. 8 and 9, comprises a body 72 defining an axial central through-cavity 74 through which beam 22 will pass in the final assembled configuration (see FIG. 5).

Cavity 74 is delimited, on either side of axis Δ, by two travel limitation surfaces 76 extending opposite to each other, symmetrically with respect to an axial plane perpendicular to the transverse direction (the vertical direction on the cross-sectional view of FIG. 5). The two symmetrical travel limitation surfaces advantageously have a variable spacing in transverse direction, increasing from proximal to radial side of the beam.

Advantageously, these variable-spacing surfaces each are surfaces without discontinuity in axial direction and define in an axial plane a continuously variable curvature homologous to a curvature followed by the beam as it bends. This travel limitation surfaces configuration allows the point of contact of beam 22 against the travel limitation surface 76 to progressively move in a direction away from the clamping part, which thus reduces the free length of the beam as the beam bends.

The advantages of such an arrangement are described in detail and quantified in particular in the above-mentioned US 2019/381325 A1, in which this geometry is described as a "duck's beak" shape.

The synthetic-material part 58 also includes a notch 78 intended to support the PCBs 62 on each side of the main axis Δ. Part 58 also includes a slot 80 giving access to axial cavity 74 by the side, in order to allow the introduction into this cavity of beam 22 already provided with its clamping 24 and its inertial mass 26 (that is to say, the beam in the configuration of FIG. 6).

Figure 10:
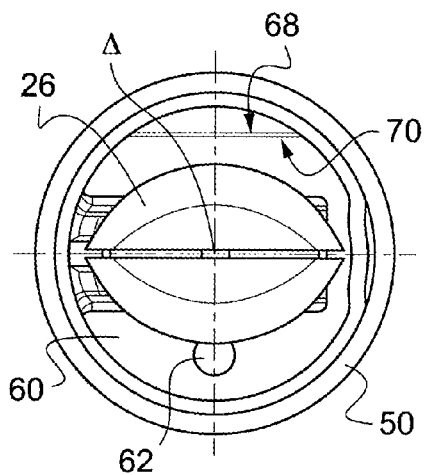
FIGS. 10 and 11 are front views of the PEH module according to the invention illustrated in FIG. 5, in configuration of neutral position of the beam and in configuration of maximum bending of the beam, respectively.
Figure 11:
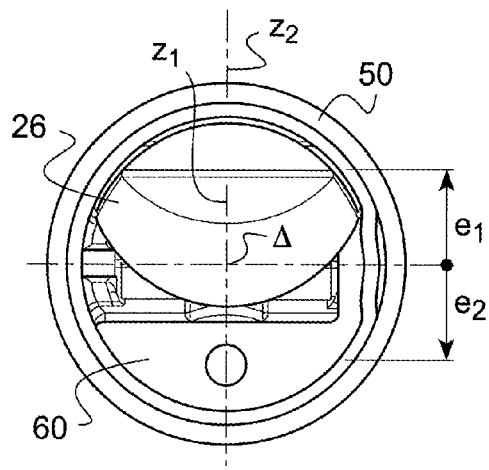
Figure 12:
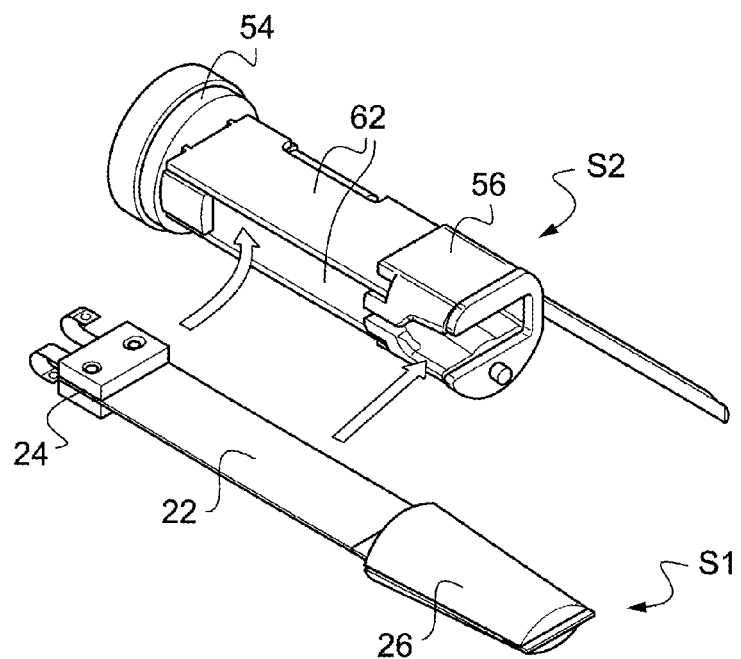
FIGS. 12 and 13 illustrate two preliminary steps of the PEH module assembly process according to the invention.

FIGS. 10 and 11 are front views of the PEH module according to the invention in its final assembled state, corresponding to the cross-sectional view of FIG. 5, respectively in configuration of neutral position of the beam (with beam 22 and inertial mass 26 extending along axis Δ) and in configuration of maximum bending of beam 22, whose free portion located just before inertial mass 26 comes into contact with one of the travel limitation surfaces 76.

When the beam is deformed under the stresses applied from the outside of the PEH module, the respective transverse axes $z_1$ and $z_2$ of inertial mass 26 and tube 50 remain aligned and merged with each other.

Moreover, the symmetrization insert 56 makes it possible, due to the very accurate positioning of the metal-material part 60 with respect to tube 50, to position very accurately the two travel limitation surfaces 76 at respective equal distances $e_1$ and $e_2$ from axis Δ, which ensures that the maximum excursion of inertial mass 26, and hence the maximum bending of beam 22, can be achieved during the pendular unit oscillations.

Figure 16:
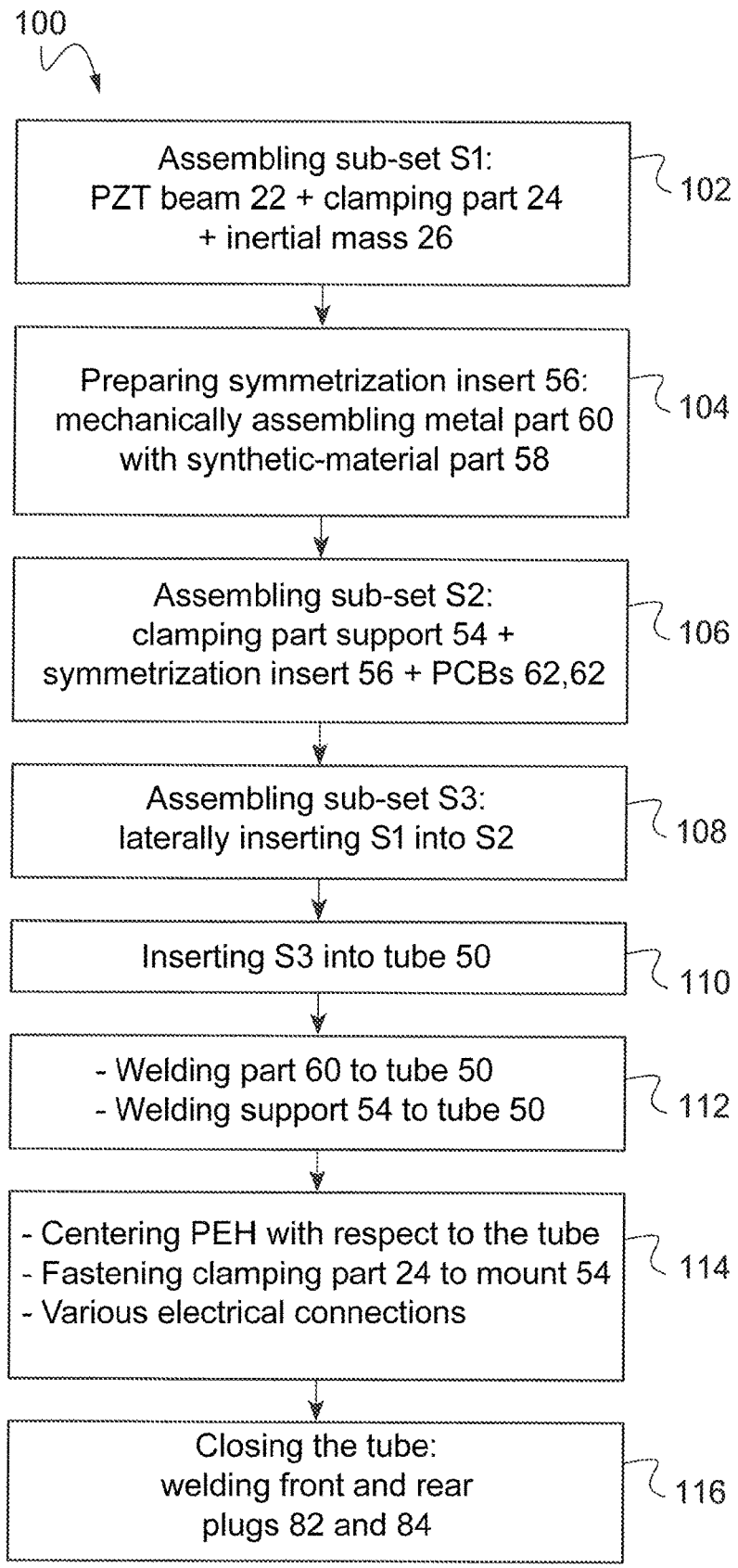
FIG. 16 is a flow diagram explaining the different steps of the assembly process illustrated in FIGS. 12 to 15.

With reference to FIGS. 12 to 15, disclosure will be made of a method for assembling the above-described PEH module, the different steps of this manufacturing method being explicitly shown in the flow chart of FIG. 16.

The first step (block 102 of the flow chart 100 of FIG. 16) consists in assembling a first sub-set S1 (FIG. 12) consisted of PZT beam 22 with clamping part 24 at its proximal end and inertial mass 26 at its distal end. This step is carried out by techniques known per se, for example that described in the above-mentioned EP 3 892 325 A1 for clamping 24, and for inertial mass 26, for example by bonding two symmetrical parts forming together a truncated cone, on either side of beam 22 in the free portion of the beam.

The following step (block 104) consists in preparing the symmetrization insert 56 by mechanically assembling metal-material part 60 to synthetic-material part 58 (FIG. 7), for example by snap-riveting the pin 62 of part 60 into the bore 64 of part 58.

Once symmetrization insert 56 built, the following step (block 106) consists in assembly a sub-set S2 (FIG. 12) gathering mount 54 and symmetrization insert 56 with the two PCBs 62 mounted between these two elements 54 and 56. It will be noted that the PCBs 62 are simply fitted at their ends into parts 54 and 56 but that, due to the residual assembly clearance and the proper flexibility of the PCBs, the sub-set S2 is not totally rigid and leaves in particular between mount 54 and symmetrization insert 56 a small margin of relative deformation in rotation and transverse and lateral translation.

The following step (block 108) consists in gathering the sub-sets S1 and S2 into a sub-set S3, by introducing beam 22 into lateral slot 80 of symmetrization insert 56 and clamping part 24 into mount 54.

Figure 13:
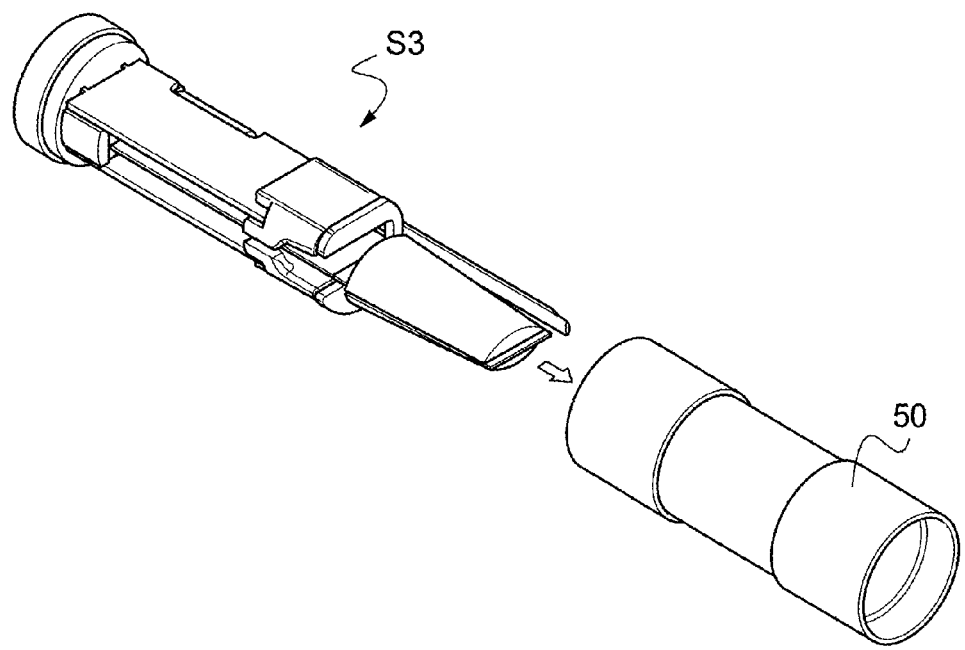
Figure 14:
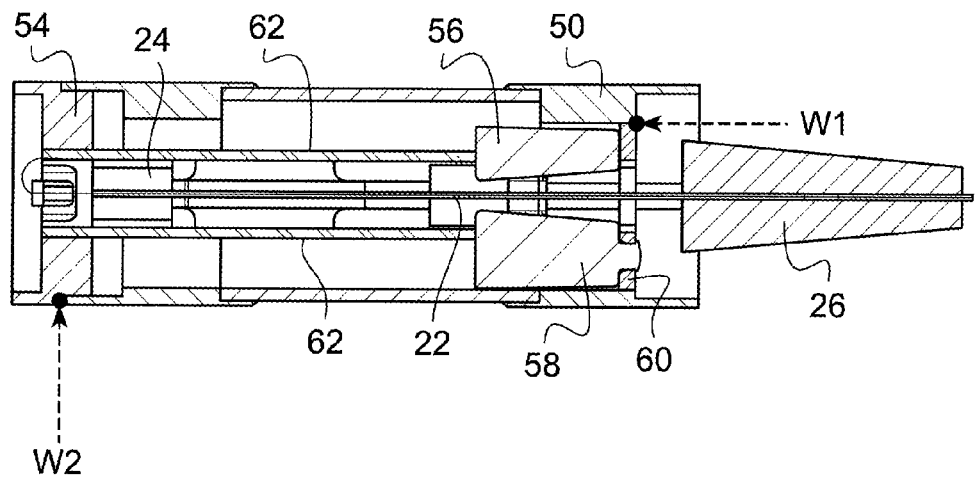
FIG. 14 illustrates, in cross-sectional view, the module obtained at the end of the steps illustrated in FIGS. 12 and 13, before the making of the final weldings of the assembly process.
Figure 15:
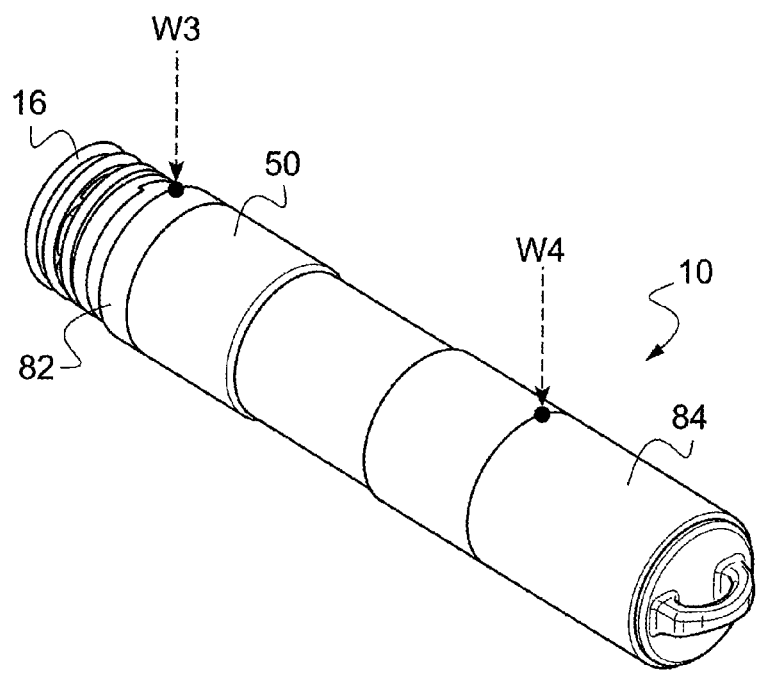
FIG. 15 illustrates the device obtained at the end of the process, after addition of the complementary parts for obtaining an implantable leadless capsule.

The following step (block 110) consists in introducing this sub-set S3 into envelop tube 50 by axial translation (FIG. 13). The result of this step is illustrated, in cross-sectional view, in FIG. 14.

The following step (block 112) consists in centering accurately symmetrization insert 56 with respect to tube 50, transversely, laterally and in rotation, by accurately adjusting metal-material part 60 of symmetrization insert 56 with respect to the housing of corresponding shape of envelope tube 50. Once this centering performed, symmetrization insert 56 is attached definitively to tube 50, advantageously by welding (as in W1) metal part 60 to the metal body of tube 50. The welding is made for example at several points by laser shots directed towards the interface between these two parts. At the end of this operation, the accurate alignment of the symmetrization insert ensures the perfectly symmetrical positioning of the travel limitation surfaces 76 on either side of axis Δ, and hence the maximum travel of the beam when the beam oscillates.

Once the symmetrization insert attached to the tube, mount 54 supporting clamping part 24 is attached to tube 50, here again advantageously by welding (as in W2) at several points by means of peripheral laser shots.

The fact that symmetrization insert 56 and mount 54 are distinct parts, and that insert 58 is attached to the tube before mount 54, results in that a potential misalignment between these two parts will have no consequence on the centering of beam 22 and inertial mass 26 with respect to tube.

This characteristic of the invention is different from the prior systems such as those described for example in above-mentioned US 2019/381325 A1, which uses a single synthetic-material multifunction part, introduced in force into the metal envelope tube, ensuring the positioning and holding of the different elements of the pendular unit.

At the following step (block 114), the PEH is centered with respect to tube 50, then clamping part 24, and hence sub-set S1, is attached to mount 54, for example by welding. This step also comprises various annex operations such as, in particular, the making of electric connections between the different elements of the implant (PCB 52, electrodes of the PZT, etc.).

The final step (block 116) consists in closing at its two ends tube 50 containing the pendular unit, by adding a front plug 82 carrying anchoring screw 16 of the leadless capsule and a rear plug 84. These plugs 82 and 84 are attached to tube 50 by peripheral weldings W3 and W4. The leadless capsule is then in its final, assembled state.

The invention claimed is:

1. An energy harvesting module, PEH, comprising:
  an elongated envelope tube;
  contained inside the tube, a pendular unit comprising:
   a piezoelectric transducer, PZT, beam, the beam extending in axial direction between a clamped proximal end and a free distal end and being elastically deformable in bending;
   an inertial mass, coupled to the free distal end of the beam and mobile in transverse direction inside the tube; and
   a beam mount, adapted to be secured to the tube and fastened to a beam clamping part at the proximal end of the beam,
  wherein the pendular unit is adapted to convert a mechanical energy produced by oscillations of the pendular unit under the effect of external stresses undergone by the module into an oscillating electrical signal collected by surface electrodes of the beam,
  wherein the module further comprises:
   a symmetrization insert, for calibrating and symmetrizing in transverse and lateral directions the pendular unit oscillations, the symmetrization insert being arranged inside the tube in a region of free travel of the beam near the inertial mass,
  wherein the symmetrization insert is distinct from the beam mount and comprises:
   a peripheral portion adapted to be secured to the tube independently of the beam mount, the tube having an inner shape mating with the outer shape of the peripheral portion at the place where the peripheral portion has to be secured; and
   a central portion with an axial through-cavity inside which the beam extends in said region of free travel, the axial cavity extending between opposite travel limitation surfaces, the travel limitation surfaces being symmetrical and being capable of coming into contact with the beam in a bending configuration of the beam.

2. The module of claim 1, wherein the symmetrization insert comprises:
  a synthetic-material element comprising said central portion of the insert; and
  a metal-material element adapted to be welded to the tube at said peripheral portion of the insert,
 wherein the synthetic-material and metal-material elements are mechanically secured to each other.

3. The module of claim 1, wherein said peripheral portion of the symmetrization insert comprises a flat surface for the positioning in axial rotation of the symmetrization insert with respect to the tube, and the tube comprises a surface mating with the flat surface of the insert.

4. The module of claim 1, wherein the symmetrization insert comprises at least one notch for holding an edge of at least one printed circuit board supported by the beam mount and by the symmetrization insert.

5. The module of claim 1, wherein the travel limitation surfaces of the central portion of the symmetrization insert have a mutual transverse spacing which increases in a direction away from the beam mount.

6. The module of claim 1, wherein the module is integrated in an autonomous device further containing, in a device body:
- an electronic unit;
- a power management circuit adapted to rectify and regulate an electric signal produced by the PEH module, outputting a stabilized direct power voltage or current; and
- an energy storage component for powering the electronic unit, said stabilized direct voltage or current provided by the power management circuit being used to power the electronic unit and/or to charge the energy storage component of the autonomous device.

7. The module of claim 6, wherein the module is integrated in an active medical device of the implantable autonomous capsule type, comprising a capsule body with an element for anchoring to a wall of a patient's organ, and wherein the external stresses to which is subjected the pendular unit of the PEH module are stresses applied to the capsule body resulting from movements of said wall and/or from flow rate variations of a flow in the surrounding environment.

\* \* \* \* \*